(12) United States Patent  
Mark et al.

(10) Patent No.: US 9,365,382 B2
(45) Date of Patent: Jun. 14, 2016

(54) INSTALLATION FOR PROCESSING A PAPER WEB OR CORRUGATED CARDBOARD WEB

(71) Applicant: BHS CORRUGATED MASCHINEN-UND ANLAGENBAU GMBH, Weiherhammer (DE)

(72) Inventors: Maximilian Mark, Tirschenreuth (DE); Achim Helgert, Georgenberg (DE)

(73) Assignee: BHS CORRUGATED MASCHINEN-UND ANLAGENBAU GMBH, Weiherhammer (DE)

( * ) Notice: Subject to any disclaimer, the term of this patent is extended or adjusted under 35 U.S.C. 154(b) by 0 days.

(21) Appl. No.: 14/768,546

(22) PCT Filed: Feb. 18, 2014

(86) PCT No.: PCT/EP2014/053108
§ 371 (c)(1),
(2) Date: Aug. 18, 2015

(87) PCT Pub. No.: WO2014/128115
PCT Pub. Date: Aug. 28, 2014

(65) Prior Publication Data
US 2016/0009516 A1 Jan. 14, 2016

(30) Foreign Application Priority Data

Feb. 21, 2013 (DE) .......................... 10 2013 202 871

(51) Int. Cl.
*B41J 29/38* (2006.01)
*B41J 11/00* (2006.01)
(Continued)

(52) U.S. Cl.
CPC *B65H 26/02* (2013.01); *B31F 1/20* (2013.01); *B31F 1/2831* (2013.01); *B41J 3/407* (2013.01);*B41J 11/0095* (2013.01); *B41J 15/04* (2013.01); *G01N 21/89* (2013.01); *G01N 21/8901* (2013.01); *G01N 21/8914* (2013.01); *B65H 2701/1762* (2013.01); *G01N 2021/8917* (2013.01)

(58) Field of Classification Search
CPC .............. G01N 21/89; G01N 21/8901; G01N 21/8903; G01N 21/8914; G01N 21/8983; G01N 2021/8917; G01N 2021/8924; B65H 63/065; B65H 26/02; B41F 33/0036
See application file for complete search history.

(56) References Cited

U.S. PATENT DOCUMENTS 6,760,102 B2 *  7/2004  Harmstorf ............ B65H 63/065
                                                356/238.1
8,419,144 B2 *  4/2013  Castillo ................ B41J 11/0035
                                                   347/16

(Continued)

FOREIGN PATENT DOCUMENTS

DE        21 06 693 A1    8/1971
DE        101 61 502 A1   6/2003
(Continued)

*Primary Examiner* — Daniel J Colilla
(74) *Attorney, Agent, or Firm* — McGlew and Tuttle, P.C.

(57) ABSTRACT

An installation for the detection of projecting material defects in a paper web or corrugated cardboard web moved in a feed direction. The device comprises a sensor device comprising a first sensor unit with a first emitter for emitting first sensor beams and a second emitter for emitting second sensor beams and with a second receiver, wherein the first sensor beams run parallel to the material surface to be monitored of the paper web or corrugated cardboard web and travel along a first signal path S1 in-between. The sensor device further has a second sensor unit comprising a second emitter for emitting second sensor beams and a second receiver, wherein the second sensor beams run parallel to the material surface and travel along a second signal path S2 in-between. The first and second sensor units are oriented in such a way that the distance between the first and second sensor beams relative to the feed direction changes along their signal paths S1, S2.

19 Claims, 4 Drawing Sheets

(51) Int. Cl.
*G01N 21/89* (2006.01)
*B65H 26/02* (2006.01)
*B31F 1/28* (2006.01)
*B41J 15/04* (2006.01)
*B31F 1/20* (2006.01)
*B41J 3/407* (2006.01)

(56) References Cited

U.S. PATENT DOCUMENTS

| | | |
|---|---|---|
| 2005/0085362 A1 | 4/2005 | Hutchinson et al. |
| 2006/0148631 A1 | 7/2006 | Protocsnak et al. |
| 2008/0238959 A1* | 10/2008 | Kato ............... B41J 11/007 347/8 |
| 2013/0300794 A1* | 11/2013 | Leighton ........... B41J 11/0005 347/16 |
| 2014/0198152 A1* | 7/2014 | Hori ............... B41J 11/0095 347/22 |

FOREIGN PATENT DOCUMENTS

| | | |
|---|---|---|
| GB | 1 291 207 A | 10/1972 |
| KR | 20070113381 A * | 11/2007 |

* cited by examiner

INSTALLATION FOR PROCESSING A PAPER WEB OR CORRUGATED CARDBOARD WEB

CROSS REFERENCE TO RELATED APPLICATIONS

This application is a United States National Phase application of International Application PCT/EP2014/053108 filed Feb. 18, 2014 and claims the benefit of priority under 35 U.S.C. §119 of German Patent Application DE 10 2013 202 871.7 filed Feb. 21, 2013, the entire contents of which are incorporated herein by reference.

FIELD OF THE INVENTION

The invention is directed to an installation for processing a paper web or corrugated cardboard web comprising a material defect detection device. Furthermore, the invention relates to a method for the detection of projecting material defects in a paper web or corrugated cardboard web, which is moved in a feed direction, by means of a material defect detection device.

In this disclosure, projecting material defects are defined as, among others, material defects which project outwards from the actual material surface, such as excessive glue, folds/creases, torn edges or web holes with projecting areas or edges, the essential criterion being that the material defect projects from the material surface.

BACKGROUND OF THE INVENTION

A large number of the most various devices for the detection of projecting material defects in moving material webs are known from prior art. In many cases, profile sensor devices are used for this purpose which are arranged above or below the material web to be monitored so as to monitor said material web from above or below. Profile sensor devices of this type need to be arranged in a horizontal cascade which makes them extremely complex and expensive. The same applies to visual monitoring systems.

Furthermore, simple light barriers are used in particular in the processing of narrow webs. These systems are however unable to detect the position of the defect. Moreover, the system often needs to be mechanically adjusted to different material web thicknesses.

Another problem of these known solutions is that false alarms occur frequently. Material defects of this type may result in severe damages during subsequent processing of the material web. The damages may occur on processing devices, on the material web itself or on the surroundings. In many cases, the material defects cause damages in particular in digital printing devices such as inkjet digital printing devices since these devices usually comprise sensitive fine ceramic components.

SUMMARY OF THE INVENTION

Therefore, it is the object of the invention to provide an installation comprising a material defect detection device that is extremely cost-effective and simple. Another object is to prevent false alarms. In particular, damages to the printing device caused by material defects shall be preventable in a simple and fail-safe manner. Yet another object of the invention is to provide a corresponding method for the detection of projecting material webs on a moved material web by means of a material defect detection device of this type.

These objects are achieved according to the invention by an installation for processing a paper web or corrugated cardboard web, the installation comprising a first supply device for supplying the paper web or corrugated cardboard web to be processed; a printing device downstream of the supply device for applying a print to the paper web or corrugated cardboard web, a device for the detection of material defects in a paper web or a corrugated cardboard web moved in a feed direction, the device comprising a sensor device with a first sensor unit comprising a first emitter for emitting first sensor beams, and a first receiver assigned to the first emitter for receiving the first sensor beams, wherein in order to detect the material defects, the first sensor beams run parallel to the material surface to be monitored of the material web and travel along a first signal path S1 between the first emitter and the first receiver; and at least one second sensor unit comprising a second emitter for emitting second sensor beams, and a second receiver assigned to the second emitter for receiving the second sensor beams, wherein in order to detect the material defects, the second sensor beams run parallel to the material surface to be monitored of the material web and travel along a second signal path S2 between the second emitter and the second receiver, wherein the first sensor unit and the second sensor unit are oriented in such a way that the distance between the first sensor beams and the second sensor beams relative to the feed direction changes along their signal paths S1, S2, and a signal evaluation unit, which is in signal communication with the first receiver and the second receiver for evaluation of the detected material defects, wherein the device for the detection of material defects in the paper web or corrugated cardboard web is arranged near the paper web or corrugated cardboard web between the first supply device and the printing device for the detection of material defects in the material web that are problematic for printing, and by a method for the detection of projecting material defects in a paper web or corrugated cardboard web moved in a feed direction, the method comprising the steps of providing a first supply device for supplying the paper web or corrugated cardboard web to be processed, providing a printing device arranged downstream of the first supply device for applying a print to the paper web or corrugated cardboard web, and providing a device for the detection of material defects in a paper web or a corrugated cardboard web moved in a feed direction, the device comprising a sensor device with a first sensor unit comprising a first emitter for emitting first sensor beams, and a first receiver assigned to the first emitter for receiving the first sensor beams, wherein in order to detect the material defects, the first sensor beams run parallel to the material surface to be monitored of the paper web or corrugated cardboard web and travel along a first signal path S1 between the first emitter and the first receiver; and at least one second sensor unit comprising a second emitter for emitting second sensor beams; and a second receiver assigned to the second emitter for receiving the second sensor beams, wherein in order to detect the material defects, the second sensor beams run parallel to the material surface to be monitored of the paper web or corrugated cardboard web and travel along a second signal path S2 between the second emitter and the second receiver, wherein the first sensor unit and the second sensor unit are oriented in such a way that the distance between the first sensor beams and the second sensor beams relative to the feed direction changes along their signal paths S1, S2, and a signal evaluation unit, which is in signal communication with the first receiver and the second receiver for evaluation of the detected material defects, wherein the device for the detection of material defects in the paper web or corrugated cardboard web is arranged near the paper web or corrugated cardboard web between the first supply device and the printing device for the detection of material defects in the material web, which are problematic in the printing process. The gist of the invention is that at least two sensor units generate sensor beams which, in order to detect a material defect, run across the material surface(s) to be monitored of the material web and have a distance from each other that varies along their signal paths in the feed direction. In other words, the first and second sensor beams are not parallel to each other. The material web is monitored from the sides. The material web is formed by the paper web or corrugated cardboard web.

Depending on the position of the material defect relative to the longitudinal edges of the material web, the material defect requires different amounts of time to pass through the first and second sensor beams. If, for example, the material defect is located at a position in the material web where the distance between the first and second sensor beams relative to the feed direction is smaller than at another position, it requires less time. The feed rate of the material web is naturally constant across its width in the feed direction. Therefore, the position of the material defect is easily determinable or calculable by means of the time required to pass through the first and second sensor beams, the feed rate and the geometric arrangement of the sensor beams relative to each other.

The converse is equally true. So if, for example, the material defect is located at a position in the material web where the distance between the first and second sensor beams relative to the feed direction is greater than at another position, it requires more time.

It is advantageous if the emitters emit pulsed sensor beams.

In a favorable embodiment, the sensor units do not change their position during operation. In other words, the orientation of the first and second sensor beams relative to each other advantageously remains the same during operation.

It is advantageous if the emitters and/or the assigned receivers are distance-adjustable relative to each other. As a result, they are easily adjustable to different widths of the material webs. A stationary arrangement of the sensor units taking into account the maximum width of the material webs is however preferred.

In a favorable embodiment, the emitters and/or the assigned receivers are adjustable in the region of the respective sensor unit in a direction perpendicular to the upper side or lower side of the material web. This allows the sensor units to be adjusted to the thickness of the material web, for example. Corresponding mounting devices are preferably provided on frame parts.

The sensor units may for example be optical sensor units, ultrasound sensor units, sound wave sensor units or the like.

It is advantageous if the sensor units are secured to a common frame.

It is expedient if the signal evaluation unit comprises at least one control device.

In an advantageous embodiment, an optical and/or acoustic signal is emitted when a material defect is detected. In addition or as an alternative thereto, the region of the material web in which the material defect is located is preferably cut out automatically. In addition or as an alternative thereto, subsequent processing installations are readjusted accordingly to prevent collision with the projecting material defect. A tracking function for material web deviations allows the compensation mechanisms described above to be synchronized with the point of time the material web defect passes through. The amount of paper waste is therefore reduced to a minimum.

The signal connection between the sensor unit and the signal evaluation unit may be wired or wireless. The signal connection allows signals to be transmitted between the sensor unit and the signal evaluation unit that correspond to the material defects.

Preferably, the material web is an endless material web.

Monitoring takes place on a material surface, which is either an upper or a lower side. Alternatively, monitoring may take place on both material surfaces.

It is expedient if the signal evaluation unit is capable of adjusting the position of the paper web or corrugated cardboard web at least in the region of the printing device and/or of the printing device in such a way as to prevent collision between the detected material defect and the printing device. To this end, the printing head or printing heads of the printing device is/are lifted off or moved further away from the material web, for example. As an alternative or in addition thereto, the course of the material web is changed in such a way that the distance between the printing head or printing heads and the material web is increased. As an alternative or in addition thereto, the printing heads are protected from the material defect by a protection device such as a seal. To this end, the protection device is preferably actuated correspondingly. The risk of causing damages to sensitive parts or components is thus preventable.

In particular, the position of the at least one printing head is adjusted when the printing head is disposed in the web region of the material defect and said printing head has a critical distance from the material web in relation to the height of the material defect. This information, which is obtainable preferably by means of a sensor but also by manual operation, is available in the signal evaluation unit. In order to coordinate this, it is advantageous if the response time of the actuating device and/or the speed of the installation is taken into account.

The first supply device is preferably a supply roll device. Other alternative embodiments are conceivable as well.

In an advantageous embodiment, the printing device is a digital printing device. Other alternative printing devices are conceivable as well.

The signal evaluation unit which detects the orientation angle of the material defect, the width of the material defect and/or in particular the position of the material defect relative to the paper web or corrugated cardboard web by means of a feed rate of the paper web or corrugated cardboard web in the feed direction and a period of time which passes between the detection of the material defect by the first sensor unit and the detection thereof by the at least second sensor unit is able to determine as well if the material defect has a problematic position or extension. Material defects located for example in a lateral edge area of the material web are usually irrelevant because the edge area will in most cases be cut off. If this is the case, it is advantageous if the signal evaluation unit does not emit an error message. Therefore, the tolerances are preferably defined such as to meet the requirements of a particular order specification.

In one embodiment, the first and/or second sensor beams run obliquely to the feed direction across the width of the paper web or corrugated cardboard web. If only the first or second sensor beams run obliquely to the feed direction, then the remaining sensor beams will be perpendicular to the feed direction.

The arrangement of the sensor units such that the first emitter and the second emitter have an emitter distance SA between each other relative to the feed direction, wherein the first receiver and the second receiver have a receiver distance EA between each other relative to the feed direction, wherein the emitter distance SA and the receiver distance EA differ from one another by at least 10%, more preferably by at least 50%, and most preferably by at least 100%, allows material defects to be localized with a high level of precision. The relationship of the emitter distances and receiver distances relative to each other is preferably selected as a function of the width of the material web.

It is advantageous if the first emitter and the first receiver and/or the second emitter and the second receiver are arranged laterally adjacent to the material web. This embodiment is extremely advantageous for practical reasons as it allows the material web to be monitored across its entire width.

The embodiment in which the first and second sensor beams form an angle W1, W2 with a vertical extending perpendicular to the paper web or corrugated cardboard web relative to the feed direction, wherein the angles W1, W2, have different absolute values, again allows defects to be localized with a high level of precision. The angles are in each case preferably between 5° and 55°, more preferably between 15° and 50°, more preferably between 20° and 45°. The angles may be identical to or different from each other. Alternatively, the first and second sensor beams form angles relative to a transverse direction perpendicular to the feed direction the absolute values of which are identical.

The sensor beam curtain generated by the first emitter and/or the second emitter generate a sensor beam curtain with first or second sensor beams, respectively, which are parallel to each other, wherein the first or second sensor beams, respectively, have different vertical distances from the material surface to be monitored of the paper web or corrugated cardboard web in order to determine the height of the detected material defects, is preferably perpendicular to the monitored material surface(s) of the material web. The first and/or second receivers are correspondingly configured to detect sensor beams having different vertical distances from the monitored material surface. If, for example, only the sensor beam closest to the material web is interrupted by a projecting material defect, this allows one to easily determine the height of the material defect. It is smaller than the vertical distance of the next sensor beam of the sensor beam curtain relative to the material web. The same applies to the other sensor beams in the sensor beam curtain. In an advantageous embodiment, "multiple light barriers" are used which are able to separately detect, for example by means of a CCD (charged coupled device), a number of sensor beams arranged one above the other. This allows one to easily change the tolerance settings for the material web projection and to set reference values for various thicknesses of the material web.

The embodiment in which the sensor beam curtain covers one or both of the material surfaces of the paper web or corrugated cardboard web ensures a simple and cost-effective monitoring of both sides of the material web.

In the embodiment in which the sensor beam curtain is configured and arranged in such a way as to run across the thickness of said paper web or corrugated cardboard web, the material web is also exposed to sensor beams coming from the side, thus allowing the thickness of the material web to be determined.

Preferably, the first and/or second sensor unit is/are configured as an optical sensor unit, with the first and/or second sensor beams being light sensor beams. This embodiment results in a particularly fail-safe sensor device. Electrical pulses are advantageously converted, by the respective emitter of the optical sensor unit, into light pulses which are converted back into electrical signals by the assigned receiver of the optical sensor unit. The electrical signals are easily evaluable by the signal evaluation unit.

The embodiment in which the signal evaluation unit converts the detected period of time that passes between the detection of the material defect by the first sensor unit and the detection of the material defect by the at least second sensor unit into path length differences for determining the position of the material defect while the feed rate of the paper web or corrugated cardboard web is being increased or reduced allows the position of the material defect to be determined even if the feed rate of the material web is increased or reduced. This conversion by integrating the distance traveled by the material defect over the time difference between the two sensor beam input times allows the length of the defect in the feed direction to be decoupled from the feed rate of the material web. When a desired minimum defect length is specified in the feed direction, the number of false alarms is reduced even more.

The embodiment in which subsequent processing devices are adjusted accordingly when a material defect is detected to prevent collision with the projecting material defect, the embodiment in which the printing device and/or the paper web or corrugated cardboard web is/are adjusted, if necessary, at least in the region of the printing device to prevent collision between the printing device and the detected projecting material defect, and the embodiment in which the printing device is protected from material webs dangerous to the printing device by means of at least one protection device result in an installation that is extremely fail-safe. In particular, it is possible to prevent damages thereto caused by critical or dangerous material defects. "Critical" or "dangerous" material defects are in particular those material defects, which are likely to cause damages to the printing device or the at least one printing head thereof due to their position, size and/or height. If necessary, the position of the paper web or corrugated cardboard or of the printing device is adjusted accordingly.

In the joining device that joins the printed material web to the corrugated second material web, the material webs are advantageously glued or welded to each other. The corrugating device is preferably a corrugating roller. Other supply devices are conceivable as well.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
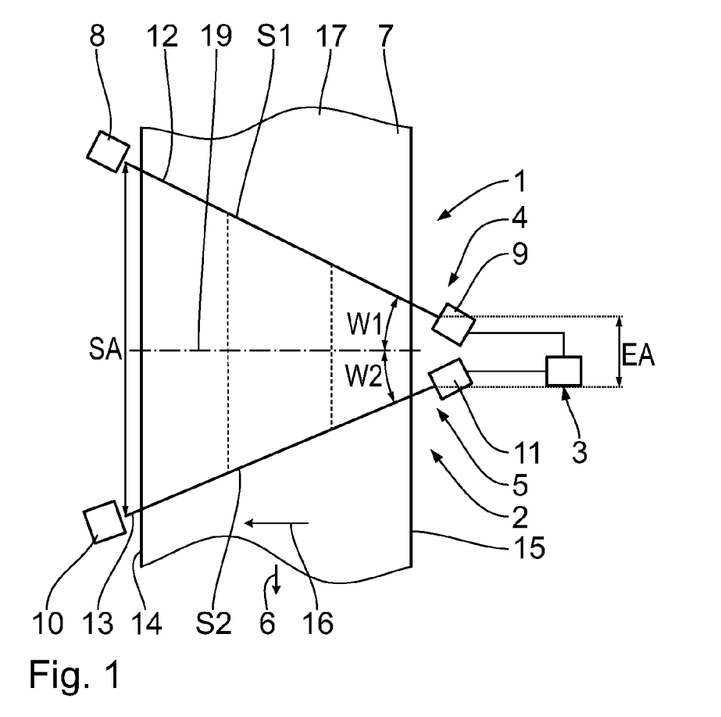
FIG. 1 is a simplified basic plan view of a device for the detection of projecting material defects according to the invention and of a material web to be monitored.
Figure 2:
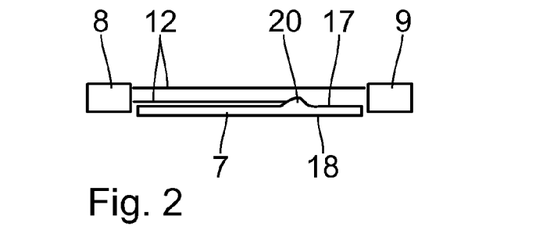
FIG. 2 is a sectional view through the device and the material web shown in FIG. 1.

Referring to FIGS. 1, 2, the following is a description of a simplified material defect detection device 1. The material defect detection device 1 comprises a sensor device 2 and a signal evaluation unit 3 which is in signal communication with the sensor device 2. The sensor device 2 in turn comprises a first sensor unit 4 and a second sensor unit 5 which is preferably identical to the first sensor unit 4. Seen in the feed direction 6 of a material web 7 to be monitored, the second sensor unit 5 is arranged downstream of the first sensor unit 4. The sensor units 4, 5 are arranged next to the material web 7. More precisely, they are in each case arranged on the sides next to the material web 7.

The first sensor unit 4 has a first emitter 8 and a first receiver 9 assigned to said first emitter 8. The second sensor unit 5 on the other hand has a second emitter 10 and a second receiver 11 assigned to said second emitter 10. The first emitter 8 emits first light sensor beams 12 which are received by the first receiver 9 if the connection between them is not interrupted. The second emitter 10 emits second light sensor beams 13 which are received by the second receiver 11 if the connection between them is not interrupted.

The material web 7 has a first longitudinal edge 14 and a second longitudinal edge 15 which is parallel to the first longitudinal edge 14. The two longitudinal edges 14, 15 extend in the feed direction 6 of the material web 7. The material web 7 further has a transverse direction 16 perpendicular to the feed direction 6 or the longitudinal edges 14, 15, respectively. In other words, the transverse direction 16 extends across the width of the material web 7. The material web 7 further has an upper side 17 and a lower side 18 opposite to the upper side 17. In this disclosure, the material web 7 is a paper web or a corrugated cardboard web. It is substantially arranged in a plane in the region of the entire sensor device 2. The material web 7 is continuously moved, by means of a feed device (not shown in FIGS. 1, 2), in the feed direction 6 at a feed rate which is usually not constant but may also be constant.

In this embodiment, the emitters 8, 10 are arranged on the side of the material web 7 next to the first longitudinal edge 14 while the receivers 9, 11 are arranged on the side of the material web 7 next to the second longitudinal edge 15. Near the first sensor unit 4, the material web 7 is located in a first plane. Near the second sensor unit 5 on the other hand, the material web 7 is located in a second plane. The first plane and the second plane may be located in a common plane; they may however also be oblique or offset to each other. In FIG. 1, the first and second planes are located in a common plane.

The first emitter 8 is arranged upstream of the second emitter 10. Between the emitters 8, 10, there is an emitter distance SA relative to the feed direction 6. The first receiver 9 is arranged upstream of the second receiver 11. Between the receivers 9, 11, there is a receiver distance EA relative to the feed direction 6. In this embodiment, the emitter distance SA relative to the feed direction 6 is greater than the receiver distance EA, preferably at least 1.1 times the receiver distance EA.

For narrow webs (width smaller than 1000 mm), the emitter distance SA relative to the feed direction 6 is considerably greater, preferably at least twice, more preferably at least three times the receiver distance EA. For wider webs (width larger than 1000 mm), the emitter distance SA relative to the feed direction 6 is between 1.1 and 1.9 times, preferably between 1.2 and 1.8 times the receiver distance EA.

According to an alternative embodiment, the receiver distance EA in the feed direction 6 is greater than, preferably at least 1.1 times the emitter distance SA. The above description concerning the distances applies conversely.

The relationship between emitter distance SA and receiver distance EA is preferably selected by taking into account the available installation space, the maximum feed rate of the material web and/or the desired resolution, in other words the precision of defect localization.

The light sensor beams 12, 13 run in each case obliquely to the feed direction 6 or the transverse direction 16. The first light sensor beams 12 form a first angle W1 with a vertical 19 to the longitudinal edges 14, 15 while the second light sensor beams 13 form an angle W2 with the vertical 19. Preferably, the angles W1, W2 are in each case between 5° and 55°, more preferably between 15° and 50°, more preferably between 20° and 45°. The angles W1, W2 may be identical to or different from each other.

The first light sensor beams 12 travel along a first signal path S1 between the first emitter 8 and the first receiver 9 while the second light sensor beams 13 travel along a second signal path S2 between the second emitter 10 and the second receiver 11.

Each of the emitters 8, 10 generates a light sensor beam curtain comprising the first or the second light sensor beams 12, 13, respectively. The first light sensor beams 12 in the first light sensor beam curtain are in each case parallel to each other and to the material web 7. They run at different vertical distances from each other. The second light sensor beams 13 in the second light sensor beam curtain are in each case parallel to each other. They run at different vertical distances from each other. The lowermost first light sensor beams 12 in the first light sensor beam curtain run vertically below and adjacent to the lower side 18 of the material web 7 in the region of the first sensor unit 4. The lowermost second light sensor beams 13 in the second light sensor beam curtain run vertically below and adjacent to the lower side 18 in the region of the second sensor unit 5. The uppermost first light sensor beams 12 in the first light sensor beam curtain run vertically above and adjacent to the upper side 17 of the material web 7 in the region of the first sensor unit 4. The uppermost second light sensor beams 13 in the second light sensor beam curtain run vertically above and adjacent to the upper side 17 in the region of the second sensor unit 5. Additional light sensor beams 12, 13 are provided between the uppermost and the lowermost first and second light sensor beams 12, 13. Since the light sensor beams 12, 13 also run across the thickness of the material web 7, the thickness thereof is determinable by means of the sensor device 2 as well.

The following is a description of the functioning of the material defect detection device 1 while in operation. The upper side 17 of the material web 7 is monitored. By means of the feed device, the material web 7 is moved at a feed rate in the feed direction. The emitters 8, 10 emit light sensor beams 12 or 13, respectively. Having traveled along the signal paths S1 or S2, respectively, the first light sensor beams 12 are received by the first receiver 9 and the second light sensor beams 13 are received by the second receiver 11 when no material defect is detected that projects from the upper side 17 of the material web 7. The signal evaluation unit 3 does not emit an error message.

It may occur that only the first receiver 9 or only the second receivers 11 does not receive all or any of the first and second light sensor beams 12, 13 at a particular point in time. In this case, there are two procedures to choose from depending on the type of material web monitoring. The results of the detection are correspondingly transmitted to the signal evaluation unit 3 which will however not emit an error message. It is then assumed that a defect has occurred. Since it cannot be localized, the defect might also be interpreted as a critical material defect.

If both the first and the second receivers 9, 11 do not receive all or any of the first light sensor beams 12 or second light sensor beams 13, respectively, at a particular point in time, the signal evaluation unit 3 will emit an error message indicating that there is a projecting material defect 20 on the upper side 17 of the material web 7.

The height of the material defect 20 perpendicular to the upper side 17 is determined by means of the light sensor beams 12 and 13 which are interrupted in the respective light sensor beam curtain. The more light sensor beams 12 or 13 are interrupted, the greater the height of the material defect 20.

The length of the material defect 20 in the feed direction 6 is determined by means of the period of time during which the first and/or second light sensor beams 12, 13 are interrupted. The feed rate of the material web 7 and the change of the feed rate over time are known.

The distance of the material web 20 from the longitudinal edges 14, 15 in the transverse direction 16 is determined by means of the period of time that passes between the interruption of the first light sensor beams 12 and that of the second light sensor beams 13. The shorter said period of time, the shorter the distance of the material defect 20 from the receivers 9, 11 which—as already described—are arranged at a smaller distance from each other in the feed direction 6 than the emitters 8, 10. The feed rate in the feed direction 6 and the change of the feed rate over time are known.

This also allows one to determine the angle of the material defect 20 relative to the longitudinal edges 14, 15 by taking into account the different maskings of the sensor beams.

Figure 3:
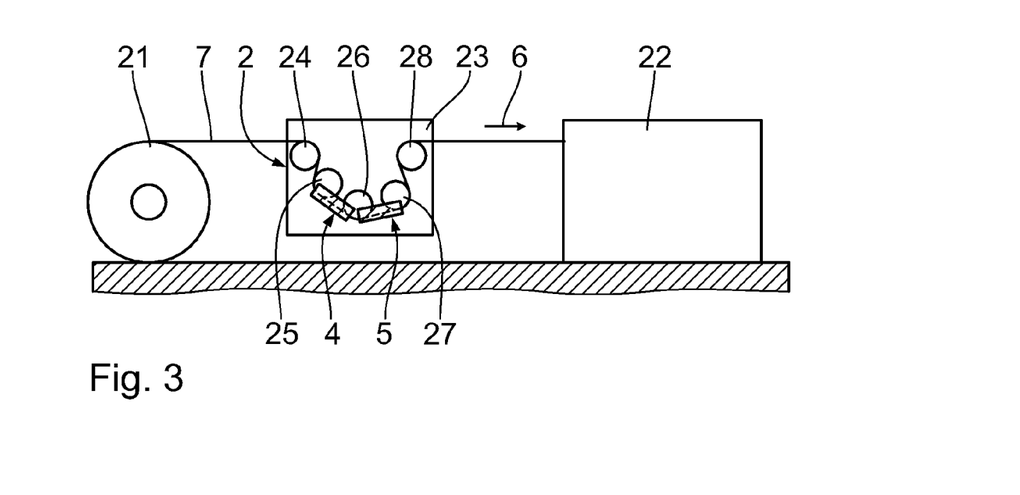
FIG. 3 is a view of a simplified installation for processing a material web, the installation substantially comprising the device shown in FIGS. 1, 2 for the detection of projecting material defects.

Referring to FIG. 3, a sensor device 2 is arranged between a supply roll 21 and a processing device 22. The basic design of the sensor device 2 corresponds to that of the sensor device 2 according to the above description to which reference is made. It is arranged downstream of the supply roll 21 the material web 7 is wound on. Via the sensor device 2, the material web 7 is moved in the feed direction 6 towards the processing device 22. The processing device 22 may be a printing device, more preferably a digital printing device, a corrugating device, a gluing device, a laminating device, a heating device, a longitudinal cutting device, a cross-cutting device, a separating device, a stacking device or the like.

The sensor device 2 is preferably arranged on a frame 23. In the sensor device 2, the material web 7 is guided around a number of rotatable deflection rollers 24 to 28. The first deflection roller 24 deflects the material web 7 downwards by approximately 90°. The second and third deflection rollers 25 and 26 are arranged downstream of the first deflection roller 24. The first sensor unit 4 for monitoring the material web 7 is arranged between these deflection rollers 25, 26.

The fourth deflection roller 27 is arranged downstream of the third deflection roller 26. The material web 7 is again deflected by the third deflection roller 26. The second sensor unit 5 for monitoring the material web 7 is arranged between the third and fourth deflection rollers 26 and 27. The measurement performed by means of the emitters 8, 10 and the receivers 9, 11 preferably takes place above the respective points of entry into the rollers 24 to 28 to prevent the measurements from being affected by oscillations of the material web 7. In contrast to the sensor device 2 according to FIGS. 1, 2, the material web 7 of the sensor units 4, 5 is disposed in different planes which are oblique to each other. Downstream of the fourth deflection roller 27, the fifth deflection roller 28 is arranged where the material web 7 is again deflected by approximately 90°, allowing the material web 7 to return to its original feed direction 6 upstream of the sensor device 2. By means of the deflection rollers 24 to 28, a controlled or higher web tension is achieved.

The lowermost first light sensor beams 12 and the lowermost second light sensor beams 13 impinge on the rolls 25, 26 or 27, respectively while the remaining first and second light sensor beams 12, 13 are arranged above the lowermost light sensor beams 12, 13 or perpendicular thereto. As a result, the first and second sensor units 4, 5 not only allow material defects 20 to be detected but also the thickness of the material web 7 to be determined.

Figure 4:
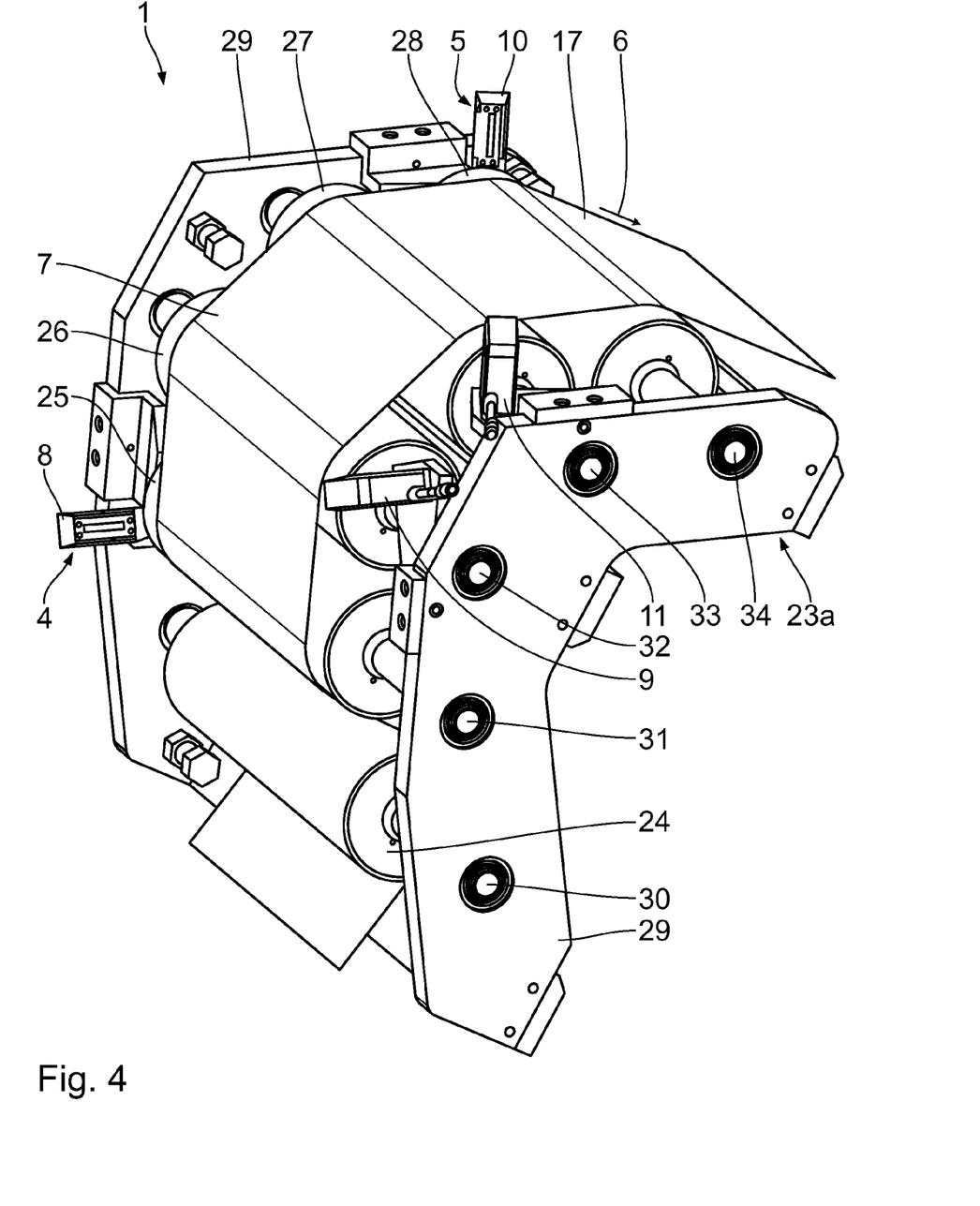
FIG. 4 is a detailed view of the device for the detection of projecting material defects substantially shown in FIG. 3.

The following is a more detailed description, with reference to FIG. 4, of a material defect detection device 1 the basic design of which corresponds to that according to FIG. 3. Identical components are designated by the same reference numerals as in the preceding embodiment to which reference is made. Structurally different components having the same functionality are designated by the same reference numerals followed by an "a". The frame 23a has two frame parts 29 which are substantially identical and parallel to each other. Each of the deflection rollers 24 to 28 has an axis 30 to 34 which are mounted for rotation in the frame parts 29 and are parallel to each other.

The material web point of entry is located at the first deflection roller 24. The material web point of exit is located at the fifth deflection roller 28. Downstream of the deflection roller 28, the material web 7 has a different direction than upstream of the deflection roller 24. The emitters 8, 10 are secured to one of the frame parts 29 while the receivers 9, 11 are arranged on the other frame part 29. The first sensor unit 4 is arranged between the second and third deflection rollers 25 and 26 while the second sensor unit 5 is arranged between the fourth and fifth deflection rollers 27 and 28.

In the region of the first sensor unit 4, the material web 7 is substantially perpendicular to the material web 7 in the region of the second sensor unit 5. Another orientation is alternatively conceivable as well.

The emitters 8, 10 are again arranged in such a way as to monitor the upper side 17 of the material web 7. The receivers 9, 11 are arranged in such a way as to receive the light sensor beams 12 and 13 which are again parallel to the material web 7 in the region of the respective sensor unit 4, 5.

The lowermost first and second light sensor beams 12, 13 are directed towards the deflection rollers 25, 26 or 27, respectively.

Figures 5, 6:
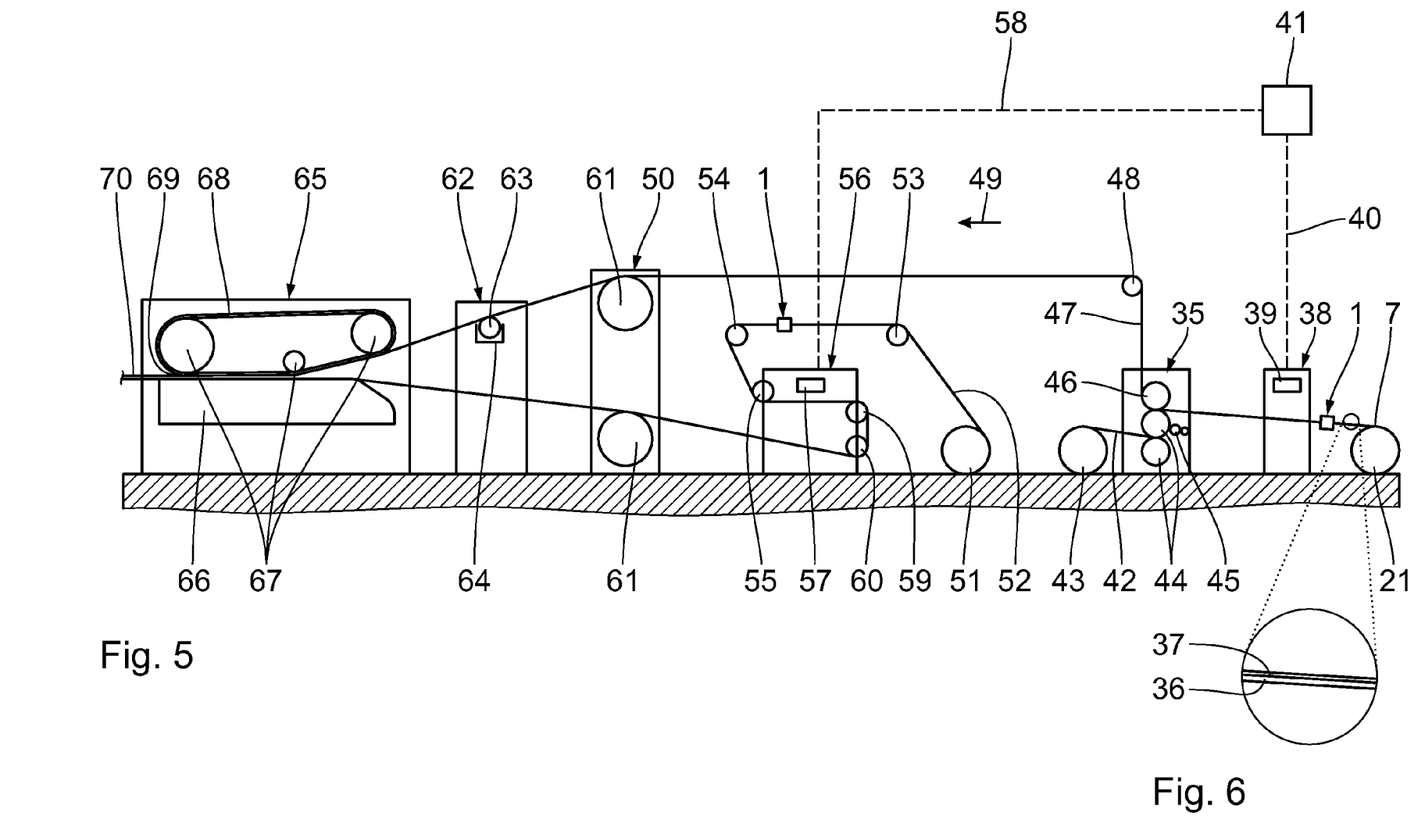
FIG. 5 is a view of a first part of a corrugated cardboard installation which comprises the device shown in FIGS. 1 to 4 for the detection of projecting material defects in a material web.
FIG. 6 is an enlarged side view of the material web.
Figure 7:
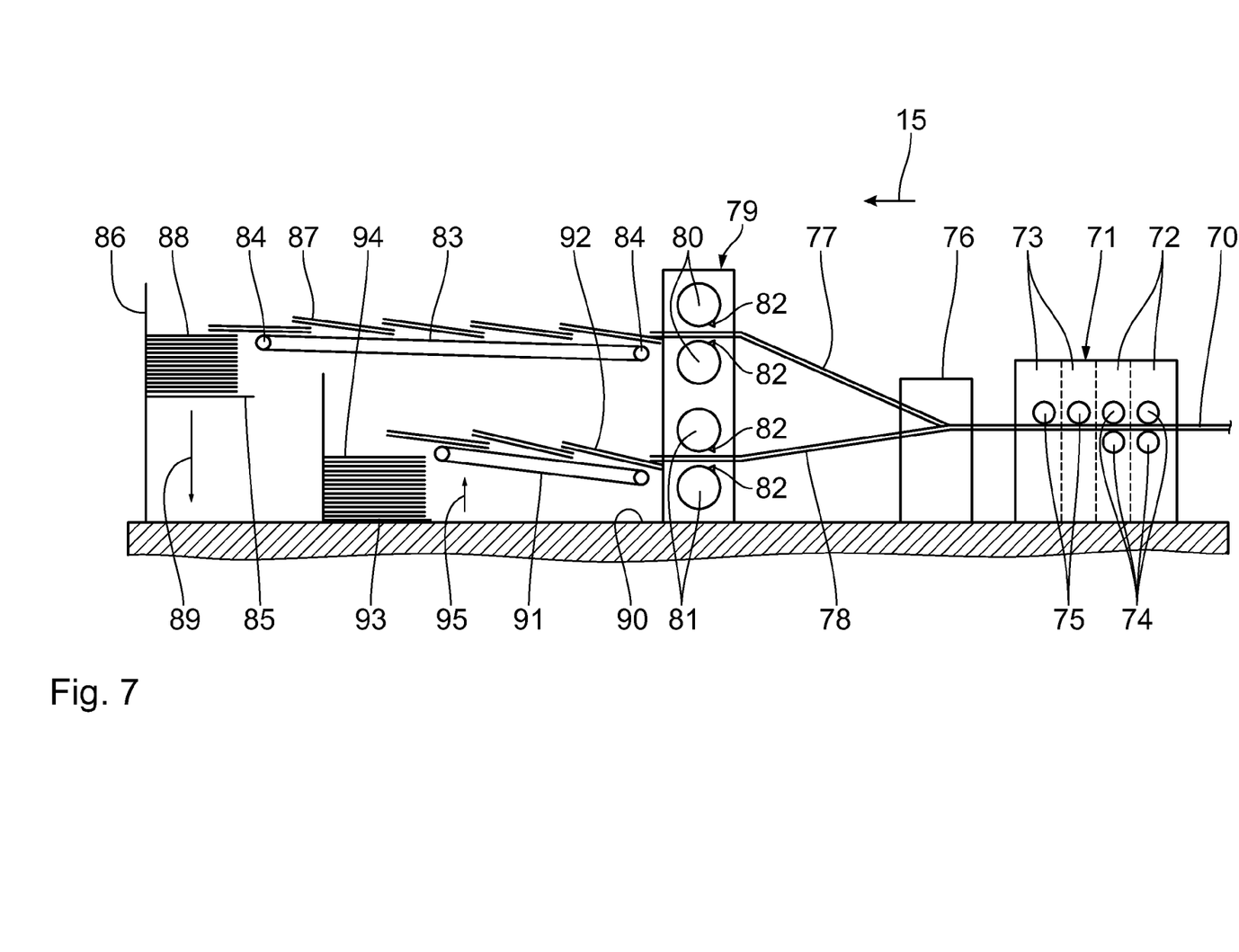
FIG. 7 is a view of a second part of the corrugated cardboard installation shown in FIG. 5.

The following is a description, with reference to FIGS. 5 to 7, of a corrugated cardboard installation which is provided with at least one material defect detection device 1 according to FIGS. 1 to 4.

The material web 7 is supplied to the machine 35 by the supply roll 21. The material web 7 is an endless paper web. The material web 7 is a base web for the corrugated cardboard produced in the machine 35. FIG. 6 shows an enlarged side view of the material web 7. The material web 7 comprises a material base layer 36 with a coating 37, a so-called primer, which increases the print quality. The thickness relationship between the material base layer 36 and the coating 37 according to FIG. 6 is not true to the actual thickness relationship. It is not necessary for the coating 37 to be applied to the material web 7 before it is wound up; it may still be applied to the material web 7 later when it has been wound off the supply roll 21.

Between the supply roll 21 and the machine 35, the material web 7 passes through a first digital printing press 38 comprising a printing head 39 by means of which a print is applied to the upper side 17 of the material 7 according to the requirements specified in a printing order. The digital printing press 38 is connected to an order control device 41 via a signal line 40.

In the machine 35, the printed material web 7 is connected to another or second material web 42 which is wound off a second supply roll 43. Having been wound off, the material web 42 is guided through adjacent corrugating rollers 44 arranged in the machine 35 in order to produce a corrugation. Having been guided through the corrugating rollers 44, the second material web 42 is in the form of a corrugated web.

Afterwards, an adhesive is applied to the tips of the corrugated material web 42 in a gluing device 45; the corrugated material web 42 is then joined to the material web 7 in the machine 35 by pressing them together in a gap between a pressing roller 46 and one of the corrugating rollers 44. As a result, a single face corrugated cardboard web 47 is obtained which is moved upwardly out of the machine 35 and deflected by a deflection roller 48 in a working direction 49. The corrugated cardboard web 47 is then moved to a preheating device 50.

A third supply roll 51 for a third material web 52 serving as an additional cover layer for the corrugated cardboard web 47 is arranged downstream of the machine 35 when seen in the working direction 49. The third material web 52 is sometimes also referred to as laminating web; in this case, the first material web 7 is referred to as cover layer.

Downstream of the second supply roll 51, the third material web 52 is at first deflected by a deflection roller 53 in such a way as to be transported in the working direction 49. Afterwards, the third material web 52 is rotated by 180° by two further deflection rollers 54, 55 in such a way that its side facing downwards between the deflection rollers 53, 54 now faces upwards, wherein downstream of the deflection roller 55, the third material web 52 is moved in a direction opposite to the working direction 49.

Downstream of the deflection roller 55, the third material web 52 passes through a second digital printing press 56 which forms a digital printing device together with the first digital printing press 38. In the second digital printing press 56, a print is applied—by means of a printing head 57—to the side of the third material web 52 facing upwards after being discharged from the deflection roller 55 according to the requirements specified in a printing order. The third material web 52 has a double-layer structure as well, comprising a base material layer and a coating in such a way that the print is applied, by means of the printing head 57 of the second digital printing press 56, to the coating of the third material web 52. The coating may also be applied to the third material web 52 after winding off and before entering the second digital printing press 56.

For controlling the printing order, the second digital printing press 56 is connected to the order control device 41 via a signal line 58. Having passed through the digital printing press 56, the third material web 52 is again deflected by substantially 180° by means of additional deflection rollers 59, 60, with the result that the third material web 52 is substantially transported in the working direction 49 again.

Downstream of the deflection roller 60, the third material web 52 is transported to the preheating device 50. The preheating device 50 comprises two heatable heating rollers 61 arranged one above the other. The corrugated cardboard web 47 and the third material web 52 move one above the other in such a way as to partly surround the respective heating rollers 61.

Downstream of the preheating device 50, a gluing device 62 is arranged which comprises a gluing roller 63 part of which is immersed in a glue bath 64. The corrugated material web 42 of the corrugated cardboard web 47 is in contact with the gluing roller 63.

Downstream of the gluing device 62, a heating and pressing device 65 is arranged which comprises a horizontal table 66 comprising heating plates, the table 66 extending in the working direction 49. An endlessly driven pressure belt 68 is provided above the table 66 which pressure belt 68 is deflected via three rollers 67.

Between the pressure belt 68 and the table 66, a pressure gap 69 is formed through which the corrugated cardboard web 47 and the third material web 52 are guided so as to be pressed together. The heating and pressing device 65 is used to produce a three-layer corrugated cardboard web 70.

FIG. 7 shows a second part of the corrugated cardboard installation after the corrugated cardboard web 70 has been discharged from the heating and pressing device 65. A longitudinal cutting and corrugating device 71 is arranged in the working direction 49 downstream of the heating and pressing device 65 which longitudinal cutting and corrugating device 71 is made of two corrugating stations 72 arranged one behind the other and two longitudinal cutting stations 73 arranged one behind the other. The corrugating stations 72 comprise corrugating tools 74 which are in each case arranged one above the other so as to form a pair through which the corrugated cardboard web 70 is guided. Each of the longitudinal cutting stations 73 comprises knives 75 which are drivable for rotation and are engageable with the corrugated cardboard web 70 to cut the corrugated cardboard web in a longitudinal direction.

Seen in the working direction 49, a separating device 76 is arranged downstream of the longitudinal cutting and corrugating device 71 to separate longitudinally cut web portions 77, 78 of the corrugated cardboard web 70 from each other. The web portions 77, 78 are then transported to a cross-cutting device 79. The cross-cutting device 79 comprises an upper pair of cross-cutting rollers 80 for the upper web portion 77 and a lower pair of cross-cutting rollers 81 for the lower web portion 78. The rollers of the pairs of rollers 80, 81 are in each case provided with a cutting bar 82 which extends radially outwards and perpendicular to the working direction 49. The cutting bars 82 of a pair of cross-cutting rollers 80, 81 interact to separate the web portions 77, 78 in a transverse direction. An upper conveyor belt 83 is arranged downstream of the upper pair of cross-cutting rollers 80 which conveyor belt 83 is deflected by rotatable rollers 84.

A deposit station 85 having a vertical stop device 86 is arranged downstream of the upper conveyor belt 83, allowing corrugated cardboard sheets 87, which have been cut from the web portion 77 by means of the cross-cutting device 79, to be deposited thereon in such a way as to form a stack 88. As indicated in FIG. 7 by a directional arrow 89, the deposit station 85 is height-adjustable. For further transport of the stack 88, the deposit station 85 may in particular be lowered down to a machine bottom 90 on which the corrugated cardboard installation is arranged.

Another lower conveyor belt 91 is arranged downstream of the lower pair of cross-cutting rollers 81, the conveyor belt 91 being used to stack corrugated cardboard sheets 92 cut from the web portion 78 by means of the cross-cutting device 79 on another deposit station 93. As shown by a directional arrow 95, the lower conveyor belt 91 may be lifted so as to be adapted to the height of the stack 94.

As already mentioned, the material defect detection device 1 is arranged in the corrugated cardboard installation.

The material defect detection device 1 is for example arranged between the supply roll 21 and the machine 35.

It is advantageously arranged between the supply roll 21 and the digital printing press 38.

In addition or as an alternative thereto, the material defect detection device 1 is preferably arranged between the supply roll 51 and the digital printing press 56.

In addition and/or as an alternative thereto, the material defect detection device 1 is arranged between the supply roll 51 and the digital printing press 56.

If the primer is applied inline, it makes sense to arrange the material web monitoring system downstream of this process step since the moisture involved in this process may result in an uneven corrugated cardboard.

According to an alternative embodiment, no third material web 52 is used. According to an alternative embodiment, further material webs are used.

While specific embodiments of the invention have been shown and described in detail to illustrate the application of the principles of the invention, it will be understood that the invention may be embodied otherwise without departing from such principles.

The invention claimed is:

1. An installation for processing a paper web or corrugated cardboard web, the installation comprising:
   a first supply device for supplying the paper web or corrugated cardboard web to be processed;
   a printing device arranged downstream of the first supply device for applying a print to the paper web or corrugated cardboard web;
   a device for detection of material defects in the paper web or the corrugated cardboard web moved in a feed direction, the device comprising a sensor device and a signal evaluation unit, said sensor device comprising a first sensor unit and at least one second sensor unit, said first sensor unit comprising a first emitter for emitting first sensor beams, and a first receiver assigned to the first emitter for receiving the first sensor beams, wherein in order to detect the material defects, the first sensor beams extend parallel to a material surface to be monitored of the material web and travel along a first signal path between the first emitter and the first receiver, said at least one second sensor unit comprising a second emitter for emitting second sensor beams and a second receiver assigned to the second emitter for receiving the second sensor beams, wherein in order to detect the material defects, the second sensor beams extend parallel to the material surface to be monitored of the material web and travel along a second signal path between the second emitter and the second receiver, wherein the first sensor unit and the at least one second sensor unit are oriented in such a way that a distance between the first sensor beams and the second sensor beams relative to the feed direction changes along the first signal path and the second signal path, said signal evaluation unit being in signal communication with the first receiver and the second receiver for evaluation of the detected material defects, wherein the device for the detection of material defects in the paper web or corrugated cardboard web is arranged near the paper web or corrugated cardboard web between the first supply device and the printing device for the detection of material defects in the material web that are problematic for printing.

2. The installation according to claim 1, wherein the signal evaluation unit detects at least one of an orientation angle of the material defect, a width of the material defect and a position of the material defect relative to the paper web or corrugated cardboard web by means of a feed rate of the paper web or corrugated cardboard web in the feed direction and a period of time which passes between the detection of the material defect by the first sensor unit and the detection thereof by the at least second sensor unit.

3. The installation according to claim 1, wherein at least one of the first sensor beams and the second sensor beams extend obliquely to the feed direction across a width of the paper web or corrugated cardboard web.

4. The installation according to claim 1, wherein the first emitter and the second emitter have an emitter distance between each other relative to the feed direction, wherein the first receiver and the second receiver have a receiver distance between each other relative to the feed direction, wherein the emitter distance and the receiver distance differ from one another by at least 10%.

5. The installation according to claim 1, wherein the first sensor beams and the second sensor beams form an angle with a vertical extending perpendicular to the paper web or corrugated cardboard web relative to the feed direction, wherein the angles have different absolute values.

6. The installation according to claim 1, wherein at least one of the first emitter and the second emitter generate a sensor beam curtain with the first sensor beams or the second sensor beams, respectively, which are parallel to each other, wherein the first sensor beams or the second sensor beams, respectively, have different vertical distances from the material surface to be monitored of the paper web or corrugated cardboard web in order to determine a height of the detected material defects.

7. The installation according to claim 6, wherein the sensor beam curtain covers the material surface or both material surfaces of the paper web or corrugated cardboard web.

8. The installation according to claim 6, wherein the sensor beam curtain is configured and arranged in such a way that in order to detect a thickness of the paper web or corrugated cardboard web, the sensor beam curtain extends across the thickness of said paper web or corrugated cardboard web.

9. The installation according to claim 1, wherein the signal evaluation unit converts a detected period of time that passes between the detection of the material defect by the first sensor unit and the detection of the material defect by the at least second sensor unit into path length differences for determining a position of the material defect while a feed rate of the paper web or corrugated cardboard web is being increased or reduced.

10. The installation according to claim 1, wherein when a material defect is detected, subsequent processing devices are adjusted accordingly to prevent collision with the projecting material defect.

11. The installation according to claim 1, wherein if necessary, at least one of the printing device and the paper web or corrugated cardboard web is/are adjusted at least in a region of the printing device to prevent collision between the printing device and the detected projecting material defect.

12. The installation according to claim 1, wherein the printing device is protected from material webs, which are dangerous to the printing device, by means of at least one protection device.

13. The installation according to claim 1, further comprising a second supply device for supplying a second material web and a corrugating device for corrugating the second material web, wherein a joining device joins the printed material web to the corrugated second material web.

14. A method for detection of projecting material defects in a paper web or corrugated cardboard web moved in a feed direction, the method comprising the steps of:
   providing a first supply device for supplying the paper web or corrugated cardboard web to be processed;

providing a printing device arranged downstream of the first supply device for applying a print to the paper web or corrugated cardboard web; and providing a device for detection of material defects in the paper web or corrugated cardboard web moved in a feed direction, the device comprising a sensor device and a signal evaluation unit, said sensor device comprising a first sensor unit and at least one second sensor unit, said first sensor unit comprising a first emitter for emitting first sensor beams, and a first receiver assigned to the first emitter for receiving the first sensor beams, wherein in order to detect the material defects, the first sensor beams extend parallel to a material surface to be monitored of the paper web or corrugated cardboard web and travel along a first signal path between the first emitter and the first receiver, said at least one second sensor unit comprising a second emitter for emitting second sensor beams and a second receiver assigned to the second emitter for receiving the second sensor beams, wherein in order to detect the material defects, the second sensor beams extend parallel to the material surface to be monitored of the paper web or corrugated cardboard web and travel along a second signal path between the second emitter and the second receiver, wherein the first sensor unit and the second sensor unit are oriented in such a way that a distance between the first sensor beams and the second sensor beams relative to the feed direction changes along the first signal path and the second signal path, said signal evaluation unit being in signal communication with the first receiver and the second receiver for evaluation of the detected material defects, wherein the device for the detection of material defects in the paper web or corrugated cardboard web is arranged near the paper web or corrugated cardboard web between the first supply device and the printing device for the detection of material defects in the material web, which are problematic in the printing process.

15. The method according to claim 14, wherein the signal evaluation unit emits an error message only if the material defect is outside variably definable tolerance limits concerning at least one of a height of the material defect and a position relative to at least one of a width and a length of the web.

16. The method according to claim 14, wherein the signal evaluation unit emits an error message when at least one of the first sensor unit and the second sensor unit detects a material defect.

17. The method according to claim 14, wherein the printing device is protected from a material defect critical to the printing device when the material defect is detected.

18. The installation according to claim 1, wherein the first emitter and the second emitter have an emitter distance between each other relative to the feed direction, wherein the first receiver and the second receiver have a receiver distance between each other relative to the feed direction, wherein the emitter distance and the receiver distance differ from one another by at least 50%.

19. The installation according to claim 1, wherein the first emitter and the second emitter have an emitter distance between each other relative to the feed direction, wherein the first receiver and the second receiver have a receiver distance between each other relative to the feed direction, wherein the emitter distance and the receiver distance differ from one another by at least 100%.

* * * * *